(12) United States Patent
Cattaneo

(10) Patent No.: US 10,058,449 B2
(45) Date of Patent: Aug. 28, 2018

(54) MEDICAL SYSTEM FOR ENDOVASCULAR TEMPERATURE CONTROL OF BLOOD, AND MEDICAL CATHETER

(71) Applicant: ACANDIS GMBH & CO. KG, Pfinztal (DE)

(72) Inventor: Giorgio Cattaneo, Karlsruhe (DE)

(73) Assignee: Acandis GmbH & CO. KG, Pfinztal (DE)

( * ) Notice: Subject to any disclaimer, the term of this patent is extended or adjusted under 35 U.S.C. 154(b) by 411 days.

(21) Appl. No.: 14/403,105

(22) PCT Filed: May 14, 2013

(86) PCT No.: PCT/EP2013/059925
§ 371 (c)(1),
(2) Date: Nov. 21, 2014

(87) PCT Pub. No.: WO2013/174676
PCT Pub. Date: Nov. 28, 2013

(65) Prior Publication Data
US 2015/0141898 A1    May 21, 2015

(30) Foreign Application Priority Data
May 22, 2012  (DE) .................. 10 2012 104 381

(51) Int. Cl.
*A61F 7/12*  (2006.01)
*A61B 17/22*  (2006.01)
(Continued)

(52) U.S. Cl.
CPC ............ *A61F 7/123* (2013.01); *A61B 17/221* (2013.01); *A61B 17/320725* (2013.01);
(Continued)

(58) Field of Classification Search
CPC .. A61B 17/320725; A61B 2017/22001; A61B 2017/22051; A61F 7/123; A61F 2007/126; A61F 2007/0054; A61F 7/12
See application file for complete search history.

(56) References Cited

U.S. PATENT DOCUMENTS 5,269,758 A * 12/1993 Taheri ................ A61F 7/123
604/96.01
5,556,408 A *  9/1996 Farhat .............. A61B 17/32072
606/159
(Continued)

FOREIGN PATENT DOCUMENTS

DE    102009056450    6/2011

OTHER PUBLICATIONS

International Search Report for PCT/EP2013/059925, English translation attached to original, Both completed by the European Patent Office dated Aug. 29, 2013, All together 8 Pages.
(Continued)

*Primary Examiner* — Christopher L Templeton
(74) *Attorney, Agent, or Firm* — Hassan Abbas Shakir; Katten Muchin Rosenman LLP

(57) ABSTRACT

A medical system for endovascular temperature control of blood and for recanalization of a blood vessel, the medical system having a catheter, a radially compressible treatment device, in particular a recanalization device, which, in the compressed state, is arranged to be longitudinally movable in the catheter and, by being released from the catheter, is radially expandable for the recanalization of the blood vessel, and a temperature control element for controlling the temperature of blood, wherein the treatment device, in particular the recanalization device, can be positioned distally with respect to the temperature control element in such a way that, during use, blood which is temperature-con-
(Continued)

trolled by the temperature control element flows to the recanalization site in the blood vessel.

11 Claims, 5 Drawing Sheets

(51) Int. Cl.
*A61B 17/221* (2006.01)
*A61B 17/3207* (2006.01)
*A61M 27/00* (2006.01)
A61B 17/32 (2006.01)
A61F 7/00 (2006.01)

(52) U.S. Cl.
CPC . *A61M 27/002* (2013.01); *A61B 2017/22001* (2013.01); *A61B 2017/22051* (2013.01); *A61B 2017/22074* (2013.01); *A61B 2017/320008* (2013.01); *A61F 2007/0054* (2013.01); *A61F 2007/126* (2013.01)

(56) References Cited

U.S. PATENT DOCUMENTS

| | | | |
|---|---|---|---|
| 6,450,987 B1 | 9/2002 | Kramer | |
| 6,537,271 B1 | 3/2003 | Murray et al. | |
| 6,645,233 B1* | 11/2003 | Ayers | A61F 7/123 607/105 |
| 6,702,783 B1 | 3/2004 | Dae et al. | |
| 6,800,068 B1* | 10/2004 | Dae | A61F 7/123 600/18 |
| 7,144,407 B1* | 12/2006 | Lasersohn | A61F 7/123 606/192 |
| 8,052,701 B1 | 11/2011 | Cox et al. | |
| 2002/0045852 A1* | 4/2002 | Saab | A61F 7/123 604/96.01 |
| 2002/0111584 A1* | 8/2002 | Walker | A61M 25/00 604/113 |
| 2002/0183691 A1* | 12/2002 | Callister | A61F 7/123 604/113 |
| 2004/0210281 A1* | 10/2004 | Dzeng | A61F 7/123 607/96 |
| 2005/0085849 A1 | 4/2005 | Sepetka et al. | |
| 2005/0107741 A1* | 5/2005 | Willard | A61F 7/12 604/113 |
| 2006/0009785 A1 | 1/2006 | Maitland et al. | |
| 2007/0208367 A1* | 9/2007 | Fiorella | A61B 17/22 606/198 |
| 2007/0250050 A1 | 10/2007 | Lafontaine | |
| 2010/0036473 A1* | 2/2010 | Roth | A61F 2/958 623/1.11 |
| 2011/0160645 A1* | 6/2011 | Sutermeister | A61B 17/32072 604/22 |
| 2011/0319754 A1 | 12/2011 | Solar et al. | |
| 2012/0265188 A1* | 10/2012 | Buchbinder | A61B 18/02 606/21 |
| 2012/0277788 A1 | 11/2012 | Cattaneo | |

OTHER PUBLICATIONS

Written Opinion for PCT/EP2013/059925, English translation attached to original, Both completed by the European Patent Office dated Aug. 29, 2013, All together 16 Pages.
German Office Action for DE 102012104381.7, dated Nov. 23, 2012, 3 Pages.

\* cited by examiner

MEDICAL SYSTEM FOR ENDOVASCULAR TEMPERATURE CONTROL OF BLOOD, AND MEDICAL CATHETER

CROSS-REFERENCE TO RELATED APPLICATION

This application is the U.S. national phase of PCT Application No. PCT/EP2013/059925 filed on May 14, 2013, which claims priority to German Patent Application No. 10 2012 104 381.7 filed on May 22, 2012, the disclosures of which are incorporated in their entirety by reference herein.

TECHNICAL FIELD

The invention relates to a medical system for endovascular temperature control of blood and for treatment of a blood vessel, more particularly for recanalization of a blood vessel, and to a medical catheter.

BACKGROUND

Recanalization devices without the possibility of temperature control are used in the medical field for restoring the blood flow in blood vessels. By way of example, the blood flow can be interrupted by blood clots, more particularly thrombi, as a result of which there is a shortage of nutrients and oxygen in the downstream tissue areas. In order to restore the supply, the blood clots are removed mechanically and/or by medication.

US 2005/0085849 A1 describes such a recanalization device which enables a mechanical removal of thrombi. To this end, the device comprises a guide wire with a distal section which, when released in a blood vessel, expands radially in a spiral or screw-like manner. Using the resulting corkscrew-like structure which is positioned distally from the blood clot by means of a catheter, the blood clot is removed by withdrawing the guide wire.

A complication arising when recanalizing a blood vessel, for example after a cerebrovascular accident, is bleeding. This is connected to the fact that the necrotic regions distally from the vascular occlusion have vessels with a degenerated vessel wall. If there is a sudden blood flow during the recanalization, which accompanies the restoration of the arterial blood pressure, distal vessels may be damaged, which can lead to bleeding. This problem occurs precisely in mechanical recanalization systems which lead to a fast recanalization of the affected vessel.

The invention is based on the object of specifying a medical system which reduces the side effects during mechanical recanalization of vascular occlusions and which moreover is suitable for the effective treatment of cerebrovascular accidents. The invention is furthermore based on the object of specifying a medical catheter which is suitable for use in such a system.

SUMMARY

According to the invention, this object is achieved by a medical system comprising the features of claim 1, alternatively by a system comprising the features of claim 14. In view of the catheter, the object is achieved by the subject matter of claim 16.

The invention is based upon the concept of specifying a medical system for endovascular temperature control of blood and for treatment of a blood vessel, more particularly for recanalization of a blood vessel.

The system comprises a supply means and a radially compressible treatment apparatus, more particularly recanalization apparatus, which, in the compressed state, is arranged in a longitudinally movable manner in the supply means and radially expandable by being released from the supply means for treating the blood vessel, more particularly for recanalizing the blood vessel. The system furthermore comprises a temperature control element for controlling the temperature of blood. The treatment apparatus, more particularly the recanalization apparatus, is positionable distally from the temperature control element in such a way that, during use, blood, the temperature of which has been controlled by the temperature control element, flows to the treatment site, more particularly to the recanalization site, in the blood vessel.

The invention combines the functions of mechanical treatment systems, more particularly mechanical recanalization systems, with the advantages of endovascular hypothermia in a single system or instrument. Therefore, there is no need to change instrument for the purposes of cooling, or, generally, for temperature control, and for the purposes of treatment, more particularly recanalization. According to the invention, both processes are performed using the same system or instrument, as a result of which the effectiveness of the treatment is improved. Here, the temperature control and the treatment, more particularly the recanalization, can be carried out simultaneously or with a time offset.

The invention is suitable not only for cooling blood, but also for warming blood (hyperthermia), i.e., in general, for the temperature control of blood. Without restricting the invention, the system is described below in conjunction with the preferred cooling of blood.

Using the combined hypothermia/recanalization system, the formation of hematomas is reduced; the latter can occur if there is vascular bleeding during the mechanical recanalization. Here, according to the invention, the blood is cooled and the vessel is mechanically widened by one and the same system, without an instrument change being necessary for this during the treatment.

Moreover, the system according to the invention makes use of further positive effects from hypothermia which are particularly beneficial, precisely in conjunction with the integrated recanalization function. Thus, endovascular hypothermia is particularly suitable for the treatment of cerebrovascular accidents since it contributes to a lengthening of the time window during the treatment. In contrast to lysis, hypothermia is also suitable for the treatment of hemorrhagic cerebrovascular accidents. Hypothermia can therefore be used as one of the first treatment measures, independently of the type of cerebrovascular accident (ischemic or hemorrhagic). Specifically, endovascular hypothermia is advantageous in that the heat transfer from the blood to the temperature control medium occurs directly in the vessel. Therefore, endovascular hypothermia effects a particularly effective heat transfer. Moreover, it is possible to generate a very local cooling effect, which in turn enables the targeted treatment of specific, locally restricted body regions in the context of the integrated recanalization function.

The invention is not restricted to recanalization systems such as stents, but rather it enables the combination of the temperature control function with mechanical treatment systems in general that are used in an endovascular setting. Specifically comprised, within the scope of the invention is a radially compressible and expandable treatment apparatus such as a flow diverter, e.g. an aneurysm stent or stent graft, thrombectomy apparatuses or occlusion apparatuses. Reference is made to the Neuro Closed Stent, produced and sold by the applicant, as a specific example of an aneurysm stent, and reference is made to the Aperio device, likewise produced and sold by the applicant, as a specific example of a thrombectomy apparatus. Aneurysm coils, which change from the stretched form into a coiled form after release are an example of an occlusion apparatus usable within the scope of the invention. The stretched form corresponds to the radially compressed state and the coiled form corresponds to the radially expanded state.

Recanalization systems such as e.g. stents are particularly preferred treatment systems.

Medical instruments for endovascular hypothermia, for example balloon catheters, are already known. Such a balloon catheter is described in U.S. Pat. No. 6,702,783. However, the known instruments only serve for cooling blood and do not serve for recanalizing blood vessels.

Moreover, the known hypothermia instruments have such large dimensions that these cannot be used for the treatment of distally situated vessels, for example in the cerebral area.

By contrast, the system according to the invention for endovascular temperature control of blood and for treatment of a blood vessel, more particularly for recanalization of a blood vessel is flexibly usable and enables also the treatment of vessels with small lumen. To this end, the system according to the invention has a treatment apparatus, more particularly recanalization apparatus, and a separate temperature control element, wherein the treatment apparatus, more particularly recanalization apparatus, is positionable in the blood vessel substantially independently of the temperature control element. The separation of functions emerging therefrom in one and the same medical system enables the optimization of the function of the respective component independently of the function of the respective other component. For example, it is therefore possible to dimension the treatment apparatus, more particularly the recanalization apparatus, in such a way that the latter can be expanded in vessels with small diameters.

During use, i.e. in the case of a released, expanded treatment apparatus, more particularly recanalization apparatus, the temperature control element is arranged proximally from the former. Since the vessel diameter most generally increases from distally to proximally, the temperature control element may have a larger diameter during use than the treatment apparatus, more particularly the recanalization apparatus. Hence the surface, which also determines the effectiveness of the temperature control element, can be optimized for heat transfer without restrictions arising for the dimensioning of the treatment apparatus, more particularly recanalization apparatus, in the process since the latter is independent of the temperature control element.

Preferred embodiments of the invention are specified in the dependent claims.

The features and advantages of the embodiments according to the invention, described in the following in conjunction with the recanalization apparatus, are also disclosed and claimed in conjunction with the treatment apparatus in general. This applies to the whole application.

For example, the recanalization apparatus can comprise a radially expandable and radially compressible grating structure, through which blood can flow in the expanded state. Such recanalization apparatuses are known per se and, in the context of the combined temperature control/recanalization system, have the advantage that the blood temperature control, in particular the blood cooling, and the recanalization of the blood vessel may occur simultaneously.

In general, the temperature of the blood can be controlled using the system prior to and after the recanalization. The temperature control during the recanalization requires a recanalization apparatus through which blood can flow in the expanded state, such as e.g. the aforementioned grating structure.

For the combined handling and actuation of the recanalization apparatus and of the temperature control element, the supply means can comprise a channel for the recanalization apparatus, which channel extends along at least one temperature control line, through which a temperature control medium can flow and which is connected to the temperature control element.

In a preferred embodiment, a supply line in the channel is arranged in a longitudinally movable manner, wherein the recanalization apparatus is arranged in the supply line in a longitudinally movable manner. What the supply line achieves is a telescoping function, by means of which the distance between the temperature control element and the recanalization apparatus can be set in a simple manner. As a result, patient specific conditions, such as vessel diameter, vessel curvature, etc., can be taken into account and distant, small-lumen vessel regions can be reached by the recanalization apparatus.

To this end, the temperature control element, which has a larger diameter than the recanalization apparatus, is placed at a position at which the blood vessel has a sufficiently large diameter. For other applications, the diameter of the temperature control element can correspond to, or be smaller than, the diameter of the recanalization apparatus. With or without a guide wire from the channel, the supply line is advanced in the distal direction into the narrow vessel regions up to the recanalization site such that the recanalization apparatus can be positioned. To this end, the recanalization apparatus is advanced in the supply line up to the recanalization site, with said supply line being withdrawn after the correct positioning of the recanalization apparatus. As a result, the recanalization apparatus is released and expanded in the radial direction, wherein the free flow cross section of the vessel is reestablished or enlarged.

Alternatively, the recanalization apparatus can be arranged directly in the channel in a longitudinally movable manner. This embodiment has a simple design and can be produced easily. Moreover, it is possible to use a smaller channel diameter.

Preferably, at least two temperature control lines are connected to the temperature control element wherein a continuous feed and return of the temperature control medium, i.e. a continuous temperature control is made possible. Alternatively, a single temperature control line can be connected to the temperature control element for a pulsatile feed and return of the temperature control medium. This simplifies the design.

If the temperature control line for the feed is arranged within the temperature control line for the return, the temperature control medium guided to the temperature control element is thermally insulated against the surrounding blood.

The temperature control element supply can be achieved by virtue of the temperature control line for the feed projecting beyond the temperature control line for the return in the distal direction, wherein a proximal end of the temperature control element is connected to the temperature control line for the return and a distal end of the temperature control element is connected to the temperature control line for the feed, wherein both connections are, in particular, fluid-tight. Hence, a receiving space is produced between the distal ends of the temperature control line for the feed and the temperature control line for the return, which receptacle space is terminated in a fluid-tight manner at the axial ends and which can be filled with the temperature control medium.

If at least one outlet opening in the temperature control line for the feed is arranged at the distal end of the temperature control element, the temperature control medium flows out at the distal end of the temperature control element and it is guided back to the proximal end of the temperature control element and, from there, into the temperature control line for the return. This achieves a temperature control or heat exchange path which is as long as possible.

Alternatively, the single temperature control line for the feed and return can project beyond the channel in the distal direction, wherein a proximal end of the temperature control element is connected to the single temperature control line and a distal end of the temperature control element is connected to the channel, wherein both connections are, in particular, fluid-tight. The advantages of this embodiment are described in conjunction with the multi-lumen supply means of the temperature control medium.

The temperature control element preferably forms a temperature control balloon, more particularly a profiled temperature control balloon, which is advantageous in that the expansion is achieved by the pressure of the temperature control medium.

A simple design of the system is achieved if the at least one temperature control line, more particularly both temperature control lines, and the channel for the recanalization apparatus are arranged coaxially.

It was found that a good positionability of the temperature control element and of the treatment apparatus, more particularly recanalization apparatus, is achieved if the maximum adjustable distance between the distal end of the supply line and the distal end of the supply means, more particularly of the channel, is from 10 cm to 30 cm, more particularly from 15 cm to 25 cm.

The invention furthermore relates to a medical catheter comprising a main line comprising at least three work lumens, wherein a first work lumen is arranged eccentrically in relation to the main line and a second and third work lumen are arranged concentrically in relation to one another. Such a catheter is suitable for use in a system as claimed in one of claim 1-12 or 14 and is disclosed in conjunction with this system, as is explained in the claims and in the description. The catheter is described independently of the system and is also suitable for other usage purposes.

The catheter is advantageous in that, as a result of the eccentric arrangement of the first work lumen, the volume of one of the two other work lumens, in particular of the second work lumen is increased. This advantage becomes important particularly in the system according to the invention if the first work lumen forms the supply means for the recanalization apparatus and the second work lumen forms one of the temperature control lines, in particular the temperature control line for the feed. Then, the flow cross section for the temperature control medium is increased.

If the temperature control line for the feed is arranged radially on the inside, this is advantageous in that ideal insulation of the temperature control medium is achieved in the temperature control line for the feed. Here, the temperature control line for the return surrounds a circumferential section of the temperature control line for the feed radially on the outside. A further or the remaining circumferential section of the temperature control line for the feed is insulated by the eccentrically arranged first work lumen, more particularly the channel.

Compared to systems in which all work lumens are arranged concentrically, the catheter according to the invention is advantageous in that the individual work lumens are fixed in terms of the position along the catheter length. By way of example, this can be achieved by virtue of the eccentrically arranged first work lumen being connected, more particularly cohesively connected, to the other work lumen.

The catheter can also be used with other systems.

BRIEF DESCRIPTION OF THE DRAWINGS

The invention is explained in more detail below on the basis of exemplary embodiments with further details, with reference being made to the attached schematic drawings. In detail.

DETAILED DESCRIPTION

Figure 1:
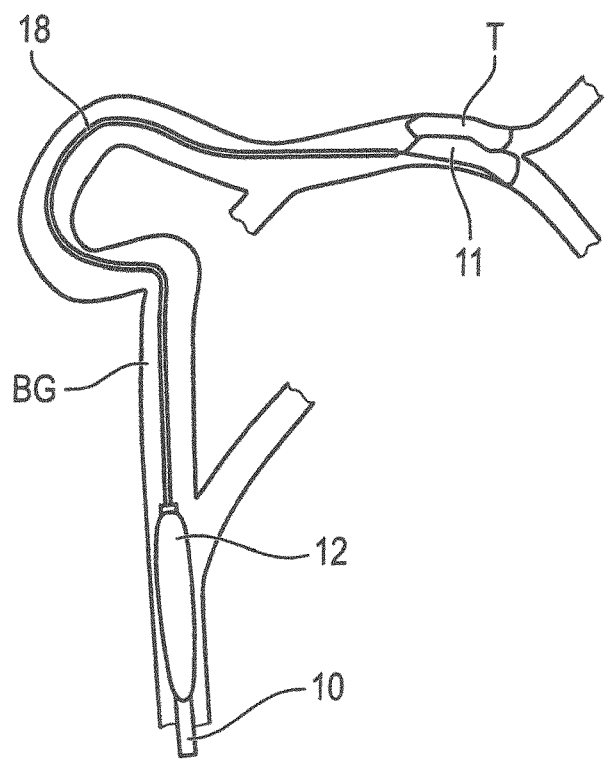
FIG. 1 shows a view of a system according to an exemplary embodiment according to the invention, in a blood vessel with an expanded recanalization apparatus, wherein, for the positioning of the recanalization apparatus, an additional supply line in a channel is provided.
Figure 2:
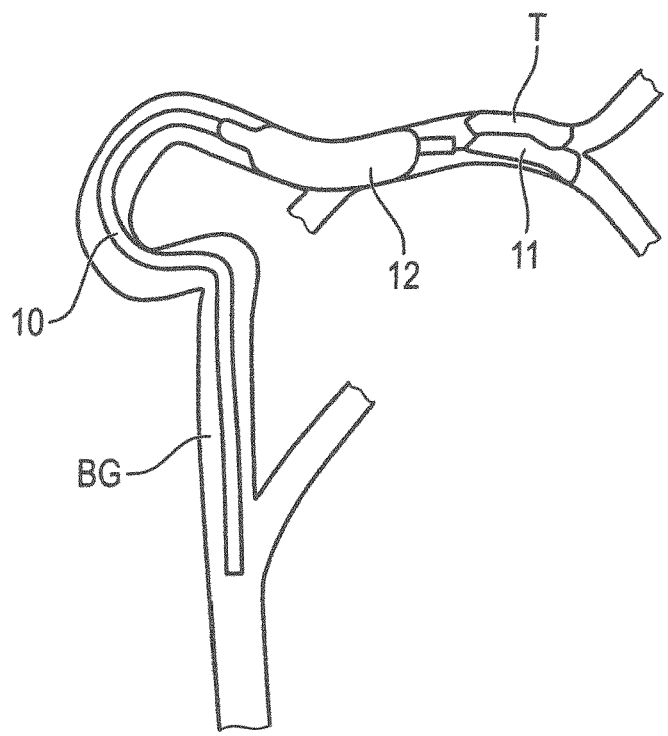
FIG. 2 shows a view of a system according to a further exemplary embodiment according to the invention, in a blood vessel with an expanded recanalization apparatus, wherein the recanalization apparatus is directly positionable by the channel without an additional supply line.

FIGS. 1 and 2 show medical systems according to examples according to the invention during use, said medical systems being inserted into a blood vessel, e.g. the carotid artery and the middle cerebral artery (MCA). The systems can be used at other treatment sites in the body.

What is common to both systems is that these combine components for endovascular temperature control of blood, in particular for endovascular hypothermia, and components for recanalization of a blood vessel in one and the same system. The system can be handled coherently such that both the cooling and the recanalization function can be satisfied during the treatment by the components of the system without an instrument change. Here, the blood cooling and the recanalization may take place independently in time from one another or simultaneously. Both systems enable the blood cooling prior to, during and after the recanalization. It is also possible, depending on the respectively selected recanalization function, to perform cooling only prior to or after the recanalization, for example if no perfusion of the vessel to be treated is possible during the recanalization process.

The invention will be described on the basis of the combined temperature control and recanalization functions. The features and advantages disclosed therewith are also disclosed and claimed in conjunction with a system which, in general, combines a temperature control apparatus with a treatment apparatus, as specified in claim 1.

For the combined cooling and recanalization, the systems as per FIGS. 1 and 2 comprise a supply means 10, more particularly a catheter, a recanalization apparatus 11 and a temperature control element 12. The recanalization apparatus 11 and the temperature control element 12 form separate components of the system, which are separated from one another spatially and in terms of function.

The recanalization apparatus 11 is radially compressible such that it is inserted on the proximal user side of the system into the supply means 10 and it is axially movable in the supply means 10 in the compressed state. As a result, the recanalization apparatus 11 can be transported through the supply means 10 to the treatment location, for example by means of a transportation wire 23 or a pusher which moves the recanalization apparatus 11.

The recanalization apparatus 11 is radially expandable when the latter is released from the supply means 10 at the treatment location, i.e. in the region of the thrombus in FIGS. 1 and 2. During the radial expansion, the diameter of the recanalization apparatus 11 increases such that the thrombus is pressed against the vessel wall and an opening is formed in the blood vessel. The radial expandability can be effected without application of an external force. In this case, the recanalization apparatus 11 is self-expandable, for example due to spring forces which are stored in the compressed state or due to the selection of a shape-memory material which is appropriately conditioned. Both mechanisms are known per se. It is also possible to expand the recanalization apparatus 11 by applying external radial forces, for example by means of a dilation catheter.

The recanalization apparatus 11 can comprise a tube-shape or stent-like grating structure which, for example is braided or a laser cut. The expansion mechanisms of such grating structures are known.

The aforementioned features of the recanalization apparatus 11 are disclosed in conjunction with all examples.

The system as per FIGS. 1 and 2 furthermore comprises a temperature control element 12, which is provided for controlling the temperature of blood. Together with the system, the temperature control means or the temperature control medium, in particular the coolant, which is part of the system, is also disclosed and claimed.

The temperature control element 12 is embodied in the form of a balloon 19. The balloon 19 is attached at the outer side of the supply means 10, in particular on the outer wall of the catheter. The supply means 10 passes through the temperature control element 12. The temperature control element 12 at least partly, more particularly completely, surrounds the supply means 10 in the circumferential direction and extends along the supply means 10 in the longitudinal direction, more particularly along a section of the supply means 10.

The temperature control element 12, in particular the balloon 19, is radially expandable. In the expanded state, the external diameter of the balloon 19 is greater than the external diameter of the temperature control line 13. Moreover, the balloon 19 is dimensioned in such a way that the latter in the target vessel has a smaller external diameter than the vessel diameter (see FIG. 1). To this end, the balloon 19 is expandable to a predetermined diameter (no compliance). During use, the blood flows through the gap between the balloon 19 and the vessel wall. To this end, the balloon 19 may have no profile, i.e. it has a smooth, continuous wall.

In order to improve the perfusion, the balloon 19 can form a profiled outer wall in the expanded state such that the blood can flow past the balloon 19 in the distal direction. Here, first wall segments of the balloon 19 may abut against the vessel wall. Second wall segments arranged therebetween may have a smaller external diameter than the first wall segments and form flow channels for the blood. By way of example, the balloon 19 may have a star-shaped cross section.

When flowing past, the blood loses heat to the balloon 19, which therefore acts as a heat exchanger.

The blood temperature-controlled or cooled in this manner then reaches the region of the recanalization apparatus 11 and, to the extent that the latter is permeable, it flows through the latter during the recanalization process. Other methods of operation are possible, as described at the outset.

The system is adapted to allow the recanalization apparatus 11 to be positioned distally from the temperature control element 12 during use. What this achieves is that, during use, blood whose temperature has been controlled by the temperature control element 12 can flow to the recanalization site. In the examples as per FIGS. 1 and 2, this is achieved by virtue of the fact that the recanalization apparatus 11 is arranged in the compressed state in the supply means 10 and can be moved in the longitudinal direction of the supply means 10. The temperature control element 12 is connected to the supply means 10, specifically to an outer wall of the supply means 12. The distal end of the temperature control element 12 ends approximately level with the distal end of the supply means 10. The distal end of the temperature control element 12 can be at a distance from the distal end of the supply means in the proximal direction. This reliably avoids a collision of the temperature control element 12 with other elements, such as e.g. the recanalization element 11, which emerge from the outlet opening provided at the distal end of the supply means 10. In other words, the temperature control element 12 extends in the proximal direction along the supply means 10, proceeding from the distal end of the supply means 10.

When the recanalization apparatus 11 is released from the supply means 10, be this directly, as in FIG. 2, or indirectly, as in FIG. 1, the recanalization apparatus 11 is situated distally from the temperature control element 12. In this manner, the sequential arrangement of the temperature control element 12 and of the recanalization apparatus 11, shown in FIGS. 1 and 2, is achieved such that blood whose temperature has been controlled by the temperature control element 12 can reach the recanalization site.

The supply means 10 is designed in such a way that it can both transport the recanalization apparatus 11 to the treatment location and supply the temperature control element 12 with a temperature control medium. To this end, the supply means 10, specifically a catheter, comprises a channel 17 for the recanalization apparatus 11. The channel 17 is described in more detail in conjunction with FIGS. 3 to 6. The channel 17 extends along at least one temperature control line 13a, 13b, through which temperature control medium flows during use and which is fluid-connected to the temperature control element 12. The supply means 10 integrates the channel 17 and the at least one temperature control line 13a, 13b into a single component, in particular in a catheter line or main line 21 such that the channel 17 and the at least one temperature control line 13a, 13b can be managed or are manageable together. The term "channel" denotes both the lumen and the wall delimiting the lumen. The same applies to the term "temperature control line".

In the following, two options are described for a possible implementation of the dual function of the supply means 10, namely the feed of the recanalization apparatus 11 and the supply of the temperature control element 12. In the example as per FIG. 1, the supply means 10 comprises a separate supply line 18, which is arranged in a longitudinally movable manner in the channel 17. The recanalization apparatus 11 in turn is arranged in a longitudinally movable manner in the supply line 18. By way of example, the supply line 18 can be embodied as a so-called micro-catheter, i.e. as a flexible catheter with a small external diameter which can advance into vessel regions with a narrow lumen. As shown in FIG. 1, this is advantageous in that the temperature control element 12 can be positioned with a relatively large distance from the thrombus T in a vessel with a comparatively large diameter. The supply line 10 is advanced from the channel 17, for example by means of a guide wire, and leaves the supply means 10. The supply line 18 is moved up to the treatment site, to be precise so far that the tip or the distal end of the supply line 18 projects beyond the thrombus T in the distal direction. The supply line 18 therefore forms a telescopable connection, in particular with two push-out segments, between the temperature control element 12 connected to the supply means 10 and the thrombus T. The recanalization apparatus 11 can then be advanced up to the thrombus T through the supply line 18 which, if the recanalization apparatus 11 is positioned correctly in the region of the thrombus, is withdrawn in a manner known per se. As a result, the recanalization apparatus 11 is released from the supply line 18, as depicted in FIG. 1, and can expand radially.

Hence, the recanalization apparatus 11 is positioned, or positionable by the system, distally from the temperature control element 12.

Alternatively, the recanalization apparatus 11 can be arranged directly in the channel 17 in a longitudinally movable manner, as depicted in FIG. 2. This simplifies the design of the system. Since the recanalization apparatus 11 expands immediately after being released from the channel 17, the distance between the temperature control element 12 and the released recanalization apparatus 11 is smaller than the distance settable with the system as per FIG. 1.

In the exemplary embodiment as per FIG. 2, the distance between the temperature control element 12 and the recanalization apparatus 11 can be set by virtue of the temperature control element 12 being withdrawn further in the proximal direction after releasing the recanalization apparatus 11, to be precise together with the supply means 10 or the catheter. During the withdrawal, the temperature control element 12 is compressed or not in the expanded state. In contrast thereto, the temperature control element 12 in the example in accordance with FIG. 1 can be positioned in a stationary manner at a suitable position of the blood vessel. The distance between the temperature control element 12 and the recanalization apparatus 11 is set by advancing the supply line 18. It is possible to see that nearly arbitrarily large distances are possible in this case. The system as per FIG. 1 is therefore particularly well-suited to recanalize occlusions in blood vessels with very small diameters and effectively cool the blood flowing to the recanalization site.

The positionability of the recanalization apparatus 11 distally from the temperature control element 12 therefore is achieved by virtue of the recanalization apparatus 11 and the temperature control element 12 being axially movable relative to one another for positioning the recanalization apparatus 11. By way of example, the relative movement can be achieved by virtue of the temperature control element 12 being arranged in a stationary manner in relation to the overall system and the recanalization apparatus 11 being moved axially directly in the supply means 10 or indirectly therein through the supply line 18. The relative movability enables the positionability of the recanalization apparatus distally from the temperature control element 12 since the recanalization apparatus can be transported via the position of the temperature control element 12 from a proximal to a distal position and can be released distally from the temperature control element 12 from the supply means 10. The relative movability between the recanalization apparatus 11 and the temperature control element 12 furthermore enables setting of the axial distance between the temperature control element 12 and the recanalization apparatus 11, as a result of which patient-specific circumstances, such as vessel diameter, vessel curvature, etc., can be taken into account.

Figure 3:
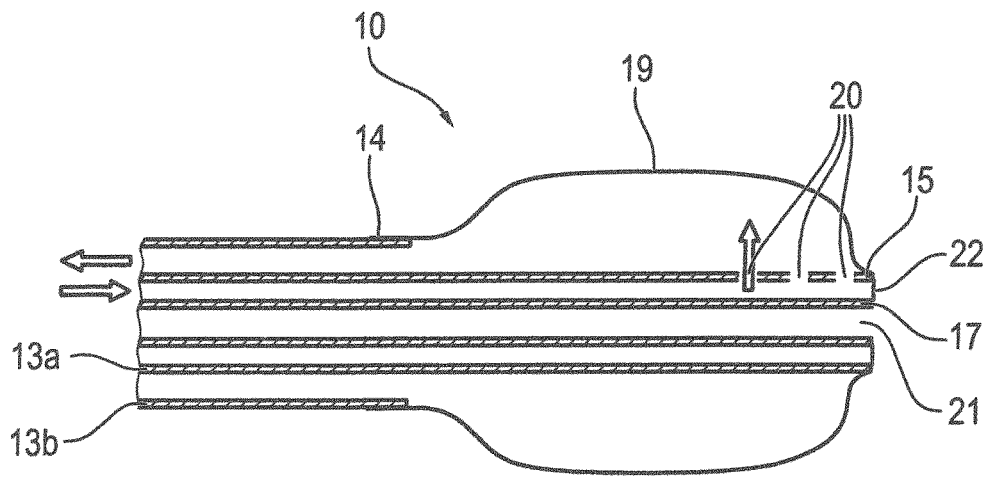
FIG. 3 shows a longitudinal section through the distal end of a catheter with three concentric work lumen, said catheter being suitable for the systems as per FIGS. 1 and 2.
Figure 4:
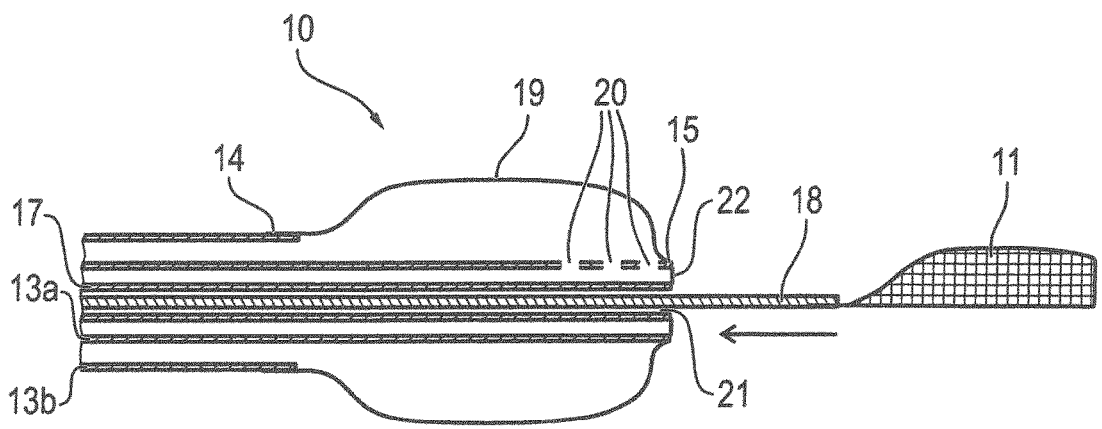
FIG. 4 shows a longitudinal section through the catheter as per FIG. 3 with a supply line in the channel in accordance with the system as per FIG. 1.
Figure 5:
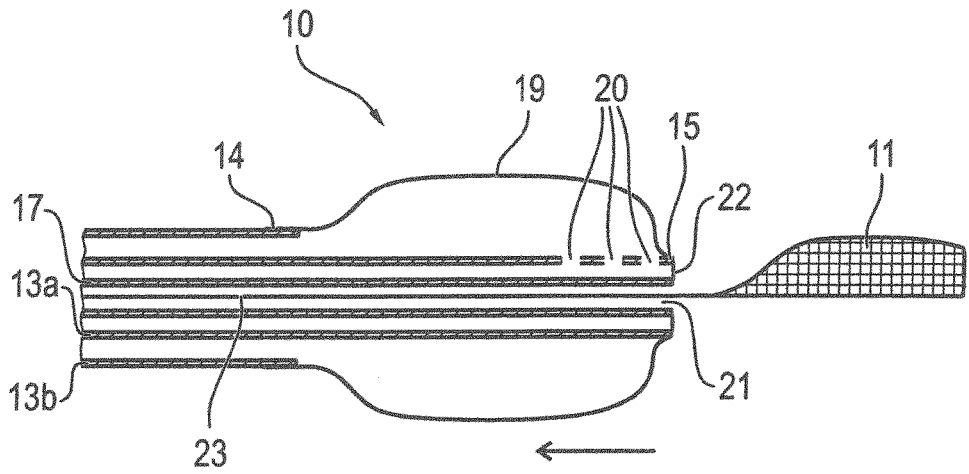
FIG. 5 shows a longitudinal section through the catheter as per FIG. 3 with a recanalization apparatus, supplied directly in the channel, in accordance with the system as per FIG. 2.
Figure 6:
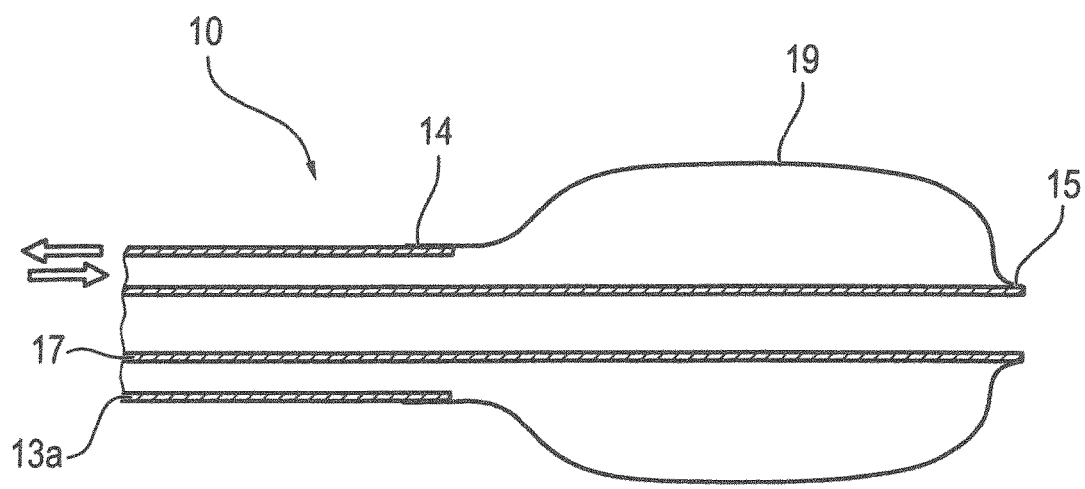
FIG. 6 shows a longitudinal section through the distal end of a catheter with two concentric work lumen, said catheter being suitable for the systems as per FIGS. 1 and 2.

Examples for the connection between the temperature control element 12 and the supply means 10 are depicted in FIGS. 3 to 6, wherein FIGS. 3 to 5 depict a three-lumen supply means 10 and FIG. 6 depicts a two-lumen supply means 10.

What is common to both supply means 10 as per FIGS. 3 and 6 is the channel 17, which is adapted for the direct supply of the recanalization element 11 (FIG. 5) or for the indirect supply through the additional supply line 18 (FIG. 4). The two supply options as per FIGS. 4 and 5 are also possible in the supply means 10 as per FIG. 6.

The channel 17 forms a flexible line or flexible tubing. The external diameter of the recanalization apparatus 11 (FIG. 5) or the external diameter of the additional supply line 18 (FIG. 4) is adapted to the internal diameter of the channel 17 such that the recanalization apparatus 11 or the supply line 18 can be moved axially within the channel 17. The same applies to the channel 17 as per FIG. 6.

The supply means 10 as per FIG. 3 has at least one further, at least two temperature control lines 13a, 13b, which extend along the channel 17. Specifically, the channel 17 and the two temperature control lines 13a, 13b are arranged substantially concentrically in the example as per FIG. 3. Other cross-sectional geometries of the supply means 10 are possible, as is explained in more detail on the basis of the exemplary embodiment as per FIG. 7.

In the example as per FIG. 3, the two temperature control lines 13a, 13b are adapted for continuous flow through the temperature control element 12, specifically through the balloon 19. To this end, one of the two temperature control lines 13a, in particular the first temperature control line 13a, serves as a feed line, through which the temperature control medium or coolant is fed to the balloon 19. The other one of the two temperature control lines, in particular the second temperature control line 13b, serves as return line, through which the temperature control medium is discharged from the balloon 19.

The first and second temperature control lines 13a, 13b are formed by flexible lines or tubing with different diameters. The inner wall of the first temperature control line 13a for the feed is formed by the outer wall of the channel 17. This results in a first annular gap between the channel 17 and the inner wall of the first temperature control line 13a, through which the temperature control medium is guided in the distal direction. Together with the inner wall of the second temperature control line 13b, the outer wall of the first temperature control line 13a forms a second annular gap, through which the heated temperature control medium is discharged from the balloon 19. The supply directions of the temperature control medium are identified by the two arrows in FIG. 3 (see also FIG. 6).

In the example as per FIG. 3, the first temperature control line 13a is situated between the channel 17 and the second temperature control line 13b. The second temperature control line 13b forms the outer wall of the supply means 10, which comes into contact with the blood during use.

The first temperature control line 13a for the feed is arranged within the second temperature control line 13b for the return. Therefore, the second temperature control line 13b is situated between the surrounding blood and the first temperature control line such that the supplied temperature control medium is thermally insulated from the blood by the returned temperature control medium.

Figure 7:
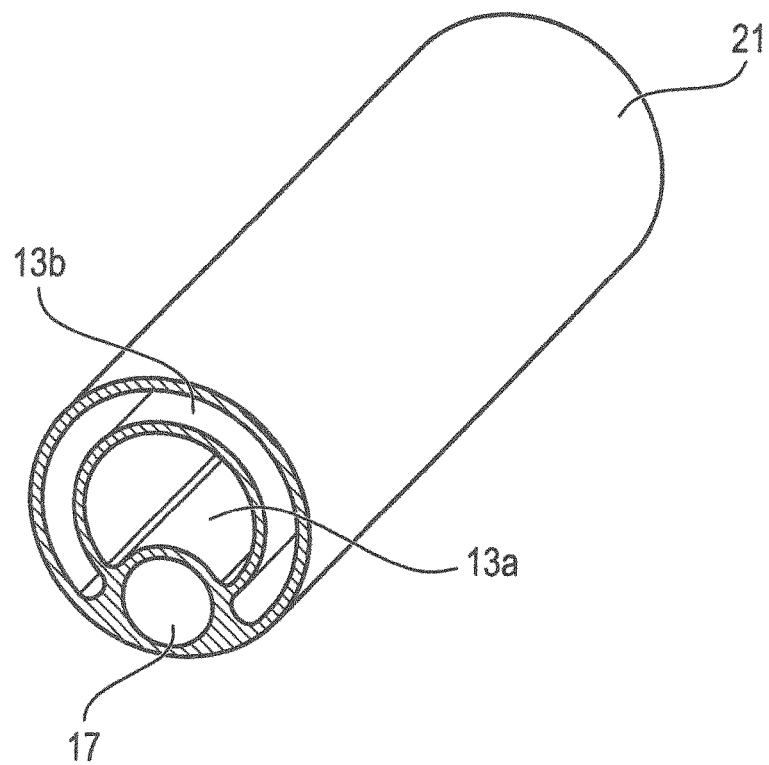
FIG. 7 shows a view of an example of a catheter according to the invention comprising three work lumen, of which one is arranged eccentrically, said catheter being suitable for the systems as per FIGS. 1 and 2.

The same insulation principle underlies the supply means 10 as per FIG. 7.

The temperature control element 12, specifically the balloon 19, has a fluid connection to the supply means 10 as follows:

The first temperature control line 13a for the feed projects beyond the distal end of the second temperature control line 13b for the return in the distal direction. Therefore, the first temperature control line 13a is—at least at the distal end of the supply means 10—longer than the second temperature control line 13b for the return. The distal end 15 of the balloon 19 is connected to the projecting section of the first temperature control line 13a for the feed, as is easy to see in FIG. 3. Specifically, the distal end 15 of the temperature control element 12 or of the balloon 19 is connected to the distal end of the first temperature control line 13a.

The distal end of the first temperature control line 13a comprises a sealing element 22 between the first temperature control line 13a and the channel 17, which prevents the temperature control medium from being able to flow out of the blood vessel. In other words, the annular gap between the channel 17 and the first temperature control line 13a is sealed distally in a fluid-tight manner by the temperature control element 12 or the balloon 19.

The proximal end 14 of the temperature control element 12 or of the balloon 19 is connected to the second temperature control line 13b in a fluid-tight manner. Specifically, the proximal end 14 of the balloon 19 is connected in a fluid-tight manner to the distal end of the second temperature control line 13b.

The fluid connection between the first temperature control line 13a and the balloon 19 is brought about by at least one outlet opening 20, for example by 2, 3 or more outlet openings 20, which are provided laterally in the wall of the first temperature control line 13a. The number and arrangement of the outlet openings 20, both in terms of the longitudinal and circumferential directions of the first temperature control line 13a, can vary from the example as per FIG. 3.

The temperature control medium leaves the balloon 19 through the annular gap between the second temperature control line 13b and the first temperature control line 13a. Therefore, the first and second temperature control lines 13a, 13b have a fluid connection to one another at the distal end, and so the temperature control medium can continuously flow through the balloon 19. The balloon 19 spans over the distance between the distal end of the first temperature control line 13a and the distal end of the second temperature control line 13b, and therefore over the projecting section of the first temperature control line 13a. Therefore, this results in a receptacle space for the temperature control medium, which is connected to the supply means 10 in a fluid-tight manner.

For an effective action of the balloon 19 as a heat exchanger, the outlet openings 20 are provided in the region of the distal end of the first temperature control line 13a such that the cool temperature control medium can flow back into the balloon 19 in the proximal direction along the projecting first temperature control line 13a. The heat transfer from the surrounding warmer blood to the cool temperature control medium in the balloon 19 occurs in the region of the balloon 19.

It is possible to set the length of the cooling stretch by means of the length of the projecting section of the first temperature control line 13a.

FIGS. 4 and 5 show different usage options of the supply means 10 or the catheter as per FIG. 3. The example as per FIG. 4 has the additional supply line 18, by means of which the supply means 10 for the supply of the recanalization apparatus 11 is telescopeable. The recanalization apparatus 11 is connected to a transport wire which is guided in the supply line 18 in such a way that the recanalization apparatus 11 is arranged in the supply line 18 in an axially movable manner. The recanalization apparatus 11 can be withdrawn back into the supply line 18 after the release. An example of a re-withdrawable mesh is published in the application 10 2009 056 450 by the applicant.

In the example as per FIG. 5, the recanalization apparatus 11 is guided directly in the channel 17. This means that the inner wall of the channel 17 keeps the recanalization apparatus 11 in the compressed state, which recanalization apparatus expands radially after release from the channel 17, as depicted in FIG. 5. The re-withdrawability of the recanalization apparatus 11 is also provided in this example, as illustrated by the arrow in the proximal direction. To this end, the transport wire 23 is actuated accordingly.

The supply means 10 as per FIG. 6 differs from the supply means 10 as per FIG. 3 in that a single temperature control line 13a is provided both for the supply and for the removal of the temperature control means, as indicated by the double-headed arrow in FIG. 6. Similar to the example as per FIG. 3, the single temperature control line 13a surrounds the channel 17, wherein the channel 17 and the temperature control line 13a are respectively embodied as flexible tubings or lines. Specifically, the channel 17 and the temperature control line 13a are arranged concentrically.

The example as per FIG. 6 is suitable for pulsatile operation, wherein the balloon 19 is alternately filled with, and emptied of, temperature control medium. To this end, the distal end 15 of the temperature control element 12, specifically of the balloon 19, is connected to the section of the channel 17 which projects beyond the distal end of the single temperature control line 13a in the distal direction. Specifically, the distal end 15 of the balloon 19 is connected to the distal end of the channel 17 in a fluid-tight manner. The proximal end of the temperature control apparatus 12, specifically of the balloon 19, is connected to the temperature control line 13a, specifically to the distal end of the temperature control line 13a. As a result, similar to the example as per FIG. 3, a cooling stretch is formed, which corresponds approximately to the length of the projecting section of the channel 17. Like in the example as per FIG. 3, the projecting section of the channel 17 is spanned by the balloon wall 19, as a result of which a receptacle space for the temperature control medium is formed. In this respect, reference is also made to the description of FIG. 3.

For supplying the temperature control element 12 with temperature control medium, the at least one temperature control line is, or both temperature control lines 13a, 13b are, connected to a supply unit (not depicted here), which is arranged extracorporeally and provides a sufficient supply pressure.

The supply means 10 forms a multifunctional catheter with a recanalization and temperature control function, in particular a cooling function.

For holding the supply line 18, the lumen of the channel 17 has a diameter of at least 0.6 mm, in particular of at least 0.7 mm, in particular of at least 0.8 mm, in particular of at least 0.9 mm, in particular of 1.0 mm, in particular of 1.1 mm, in particular of 1.2 mm, in particular of 1.4 mm. As a result of this, a substantially frictionless axial displaceability of the supply line 18, in particular of the micro-catheter, is achieved. The maximum internal diameter of the channel 17 is 1.6 mm, in particular 1.4 mm, in particular 1.2 mm, in particular 1.0 mm, in particular 0.8 mm. The aforementioned upper limits are respectively disclosed with the aforementioned lower limits for forming ranges, i.e. the upper limit 1.6 mm with all lower limit values, the upper limit of 1.4 mm with all lower limit values, etc. What the upper limit values bring about is that the supply line 18 in the channel 17 substantially does not undulate if different supply lines 18, accordingly adapted to the channel 17, are used.

The lumen of the channel 17 as per FIGS. 2 and 5, in which the recanalization apparatus 11 is guided directly in the channel 17, has a minimum diameter of 0.35 mm, in particular of 0.40 mm, in particular of 0.45 mm, in particular of 0.5 mm, in particular of 0.6 mm, in particular of 0.7 mm. What this achieves is the supply of the recanalization apparatus 11 without substantial friction. The maximum internal diameter of the channel 17 is 1.0 mm, in particular 0.9 mm, in particular 0.8 mm, in particular 0.7 mm, in particular 0.6 mm, in particular 0.5 mm. The aforementioned upper limits are in each case disclosed individually, together with the aforementioned lower limits, i.e. the upper limit of 1.0 mm is disclosed together with all lower limit values, the upper limit of 0.9 mm is disclosed together with all lower limit values, etc. The setting the maximum internal diameter brings about is that the transport or guide wire of the device does not substantially undulate in the lumen.

The individual components of the system, i.e. the supply means 10, the recanalization apparatus 11 and the temperature control element 12, form essential elements of the invention. By way of example, it is possible to offer separately the supply line 18 and the recanalization apparatus 11 on the one hand and the supply means 10 with the temperature control element 12 on the other hand, wherein the combination of these components to form the medical system is brought about differently.

Figure 8:
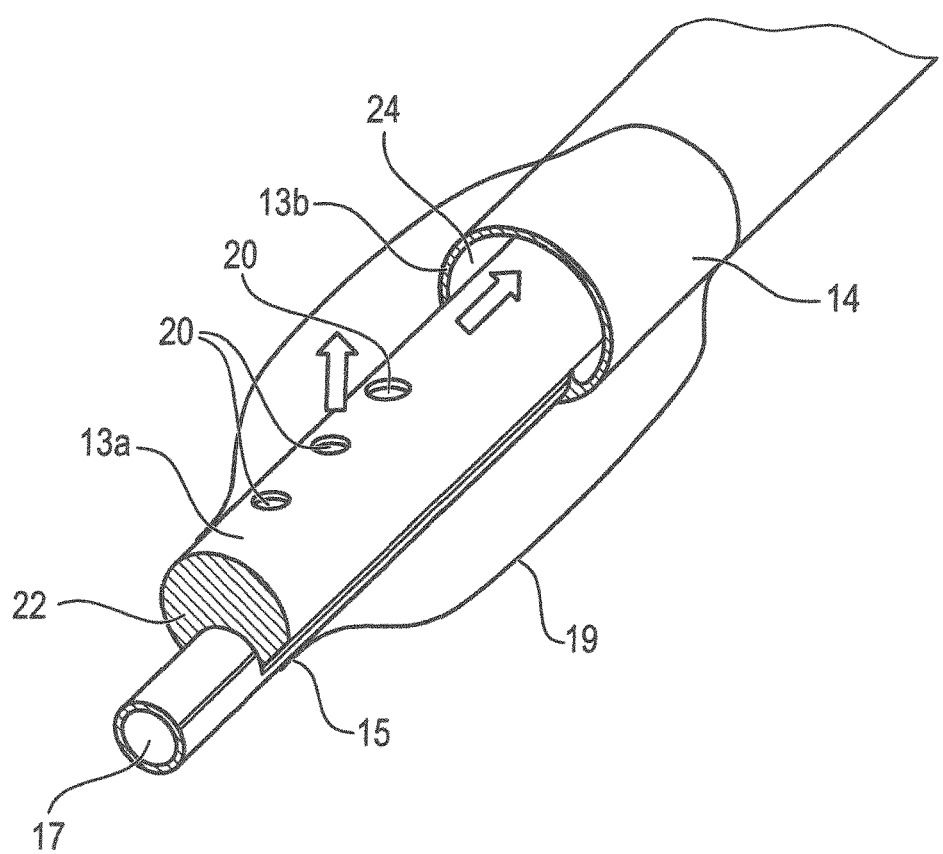
FIG. 8 shows a perspective view of the distal end of the catheter as per FIG. 7.
Figure 9:
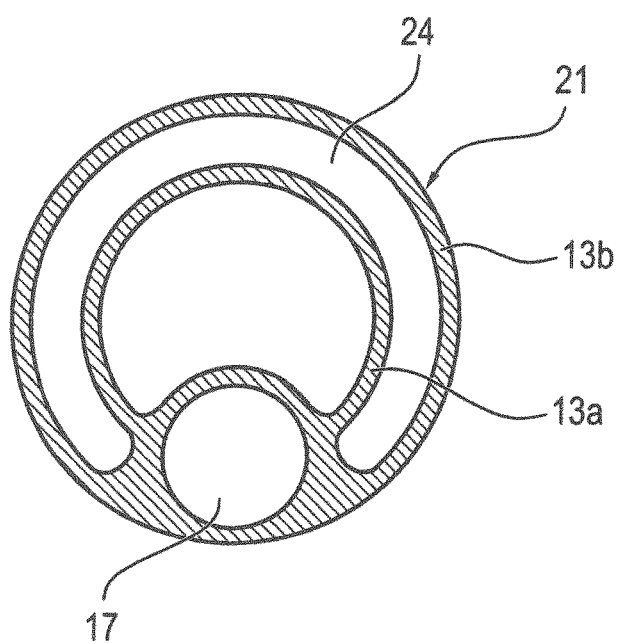
FIG. 9 shows a section through the catheter as per FIG. 7.

An example of a catheter according to the invention is depicted in FIGS. 7 to 9. The catheter shown there is disclosed in conjunction with the claimed medical system, described above, for temperature control and recanalization. It is also possible to use the catheter for other treatments with other systems. The catheter is therefore also claimed independently of the above-described system.

The catheter as per FIG. 7 forms a main line 21, which constitutes the external jacket of the catheter. At least three work lumen 13a, 13b, 17 are formed in the main line 21. More than three work lumens are possible. In the example as per FIG. 7, exactly three work lumen 13a, 13b, 17 are provided. The first work lumen 17 is arranged in an eccentric manner in relation to the center line of the main line 21. The main line 21 is tubular and has a center line (not depicted) in the center. In relation to this center line, the first work lumen 17 is arranged in an eccentric manner, as can be seen in FIG. 7. In other words, the work lumen 17 is embodied laterally, i.e. radially offset, on the wall of the main line 21. The work lumen 17 has a substantially circular cross section.

The work lumen 17 corresponds to the channel 17 in the examples as per FIGS. 1 to 6. During use, the recanalization apparatus 11 or the supply line 18 is arranged and moved in the channel 17 or in the work lumen 17.

The main line 21 has a second and third work lumen 13a and 13b. As can be seen in FIG. 7, the second and third work lumens 13a, 13b are arranged substantially concentrically with respect to one another. The second and third work lumens 13a, 13b can be embodied concentrically in relation to the main line 21 or concentrically with respect to one another if the main line 21 corresponds to the third work lumen 13b.

Specifically, the cross sections of the second work lumen 13a and of the third work lumen 13b have substantially the same center point. The second and third work lumens 13a, 13b have a substantially circular cross section, as can easily be identified in FIG. 9. The circular geometry of the second and third work lumens 13a, 13b is interrupted by the first work lumen 17 in the circumferential direction, as can be identified in FIG. 9. The second and third work lumen 13a, 13b are respectively connected, in particular cohesively connected, to the first work lumen, resulting in a positionally secured arrangement of the lumen with respect to one another.

The second and third work lumen 13a, 13b correspond to the first and second temperature control lines 13a, 13b of the examples as per FIGS. 1 and 6. The second work lumen 13a or the first temperature control line 13a serves to supply the temperature control medium to the temperature control element 12. The third work lumen 13b or the second temperature control line 13b serves for the return of the temperature control medium from the temperature control element 12. Like in the preceding examples, an annular gap 24 is formed between the second outer temperature control line 13b and the first inner temperature control line 13a. The annular gap 24 is interrupted by the wall of the eccentrically arranged channel 17. In contrast to the exemplary embodiments as per FIGS. 1 to 6, in which all lines, or the line and the channel, are arranged concentrically, resulting in a completely circumferential annular gap, the annular gap in the example as per FIG. 9 has an interrupted or crescent-shaped or C-shaped embodiment.

The advantage of the catheter as per FIGS. 7 to 9 consists of the fact that the cross-sectional area of the first temperature control line 13a is increased as a result of the eccentrically arranged channel 17. Moreover, the inlet lumen in the first temperature control line of 13a is thermally insulated against the surrounding warmer blood by the outlet lumen of the second temperature control line 13b, as a result of which the thermal transfer along the catheter between the cooling liquid, or, in general, the temperature control medium, and the blood is reduced.

The first work channel 17 is suitable for supplying a guide wire or, as mentioned, for supplying a micro-catheter. The lumen of the first work lumen or the channel 17 has a maximum diameter of 1.2 mm, in particular of 1.0 mm, in particular of 0.9 mm, in particular of at most 0.85 mm, in particular of at most 0.8 mm, in particular of at most 0.75 mm. The lower limit of the diameter is at least 0.4 mm, in particular at least 0.5 mm, in particular at least 0.6 mm, in particular at least 0.7 mm, in particular at least 0.8 mm. The aforementioned lower limits can in each case be combined individually with the aforementioned upper limits for forming ranges, for example 0.4 mm with all upper limit values, 0.5 mm with all upper limit values, etc. The aforementioned upper and lower limit values of the diameter apply to the channel 17 if the latter is designed for supplying an additional supply line 18 or a micro-catheter.

If the first work lumen 17 or the channel 17 is provided for supplying a guide wire, the first work lumen 17 has a maximum diameter of at most 1.0 mm, in particular at most 0.8 mm, in particular at most 0.6 mm, in particular at most 0.5 mm, in particular at most 0.45 mm, in particular at most 0.4 mm, in particular at most 0.35 mm. The lower limit of the diameter is at least 0.3 mm, in particular at least 0.4 mm, in particular at least 0.5 mm, in particular at least 0.6 mm. The aforementioned lower limit values can in each case be combined with all upper limit values, for example 0.3 mm with all upper limit values for supplying the guide wire, 0.4 mm with all upper limit values for supplying the guide wire, etc.

The external diameter of the catheter, specifically the external diameter of the main line 21, which, in the example as per FIG. 7 corresponds to the outer wall of the second temperature control line 13*b*, can have the following dimensions: the maximum external diameter can be 4.0 mm, in particular at most 3.5 mm, in particular at most 3.0 mm, in particular at most 2.7 mm, in particular at most 2.4 mm, in particular at most 2.0 mm, in particular at most 1.7 mm. Particularly suitable are catheters with a size of approximately 8 Fr (i.e. 2.7 mm) are suitable for the supply in the common carotid artery.

If the catheter, like in the example as per FIG. 2, is intended to be supplied further distally, an external diameter of at most 1.4 mm to 1.0 mm is possible. The lower limits, which can be respectively individually combined with the aforementioned upper limits, are at least 0.7 mm, in particular at least 1.0 mm, in particular at least 1.3 mm, in particular at least 1.7 mm.

The walls of the two temperature control lines 13*a*, 13*b* and of the channel 17 in the region of the first temperature control line 13*a* can be at most 400 µm, in particular at most 300 µm, in particular at most 200 µm, in particular at most 150 µm, in particular at most 100 µm. By way of example, the lower limit can be 90 µm.

The connection of the temperature control element 12, specifically of the balloon 19, with the catheter as per FIG. 7 is depicted in FIG. 8. In principle, the connection is brought about in a similar manner to the exemplary embodiment as per FIG. 3. In this respect, reference is made to the explanations in relation to the example as per FIG. 3, which are also disclosed in conjunction with the example as per FIG. 8.

The first temperature control line 13*a* or the second work lumen 13*a* projects beyond the distal end of the second temperature control line 13*b* or of the third work lumen 13*b* in the distal direction. The annular gap between the first temperature control line 13*a* and the second temperature control line 13*b* for the return (see the arrow in the distal direction) is easily identifiable. A plurality of outlet openings 20 are, in particular at least one outlet opening 20 is, provided in the wall of the first temperature control line 13*a*, wherein the temperature control medium can flow out of the first temperature control line 13*a* through said outlet openings (see arrow). The outlet openings 20 are arranged in the region of the distal end of the first temperature control line 13*a*. The outlet openings 20 are arranged in succession in the longitudinal direction, wherein the outlet opening 20 arranged furthest in the proximal direction is provided approximately in the center of the projecting section of the first temperature control line 13*a*.

The proximal end of the temperature control element 12, specifically of the balloon 19, is connected in a fluid-tight manner to the projecting part of the first temperature control line 13*a*, specifically to the distal end of the first temperature control line 13. The proximal end of the balloon 19 is connected in a fluid-tight manner to the second temperature control line 13*b*, in particular in a fluid-tight manner to a distal end of the second temperature control line 13*b*. Hence, a receptacle space is spanned by the balloon 19, which extends along the projecting part of the first temperature control line 13*a* and through which temperature control means can flow.

The distal termination by the sealing element 22 of the first temperature control line 13*a* is easy to identify in FIG. 8. The channel 17 or the first work lumen 17 projects beyond the distal end of the first temperature control line 13*a* in the distal direction. It is also possible for the channel 17 to end level with the first temperature control line 13*a*.

It is possible for the work lumen 13*a*, 13*b* to experience a change in the cross section in the longitudinal direction of the catheter. By way of example, the catheter may enlarge in the proximal direction such that the pressure losses in the fluid supply are reduced. The diameters specified above relate to the distal region of the catheter with a length of at least 10 mm, in particular at least 15 mm, in particular at least 20 mm, in particular at least 30 mm. The upper limit of the distal region has a length of at most 60 mm, in particular at most 50 mm, in particular at most 40, in particular at most 30 mm. The aforementioned upper and lower limits can respectively be combined with one another to form ranges.

The above-described catheter as per FIGS. 7 to 9 is disclosed and claimed in conjunction with a system as a supply lumen for a micro-catheter or a guide wire (channel 17) and as inlet lumen and outlet lumen for a coolant, wherein the coolant moves in the distal direction in the inlet lumen and in the proximal direction in the outlet lumen.

Thermoplastics, such as Pebax or PU, with or without metal reinforcement, can be considered as materials.

Furthermore, what is described is a system for the temperature control, in particular for cooling, of blood, which comprises a multi-lumen catheter with a temperature control element, as described above, and a supply line 18 in the channel 17. In contrast to the aforementioned examples, the system does not have a recanalization apparatus. Rather, the supply line 18 is adapted to supply a thrombus-detaching medicament to the blood vessel and, to this end, is connected to a suitable medicament supply.

Figure 10:
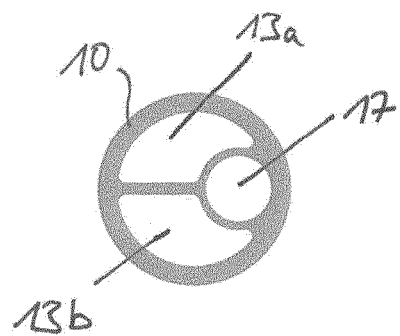
FIG. 10 shows a section through a further catheter which is suitable for the systems as per FIGS. 1 and 2.
Figure 11:
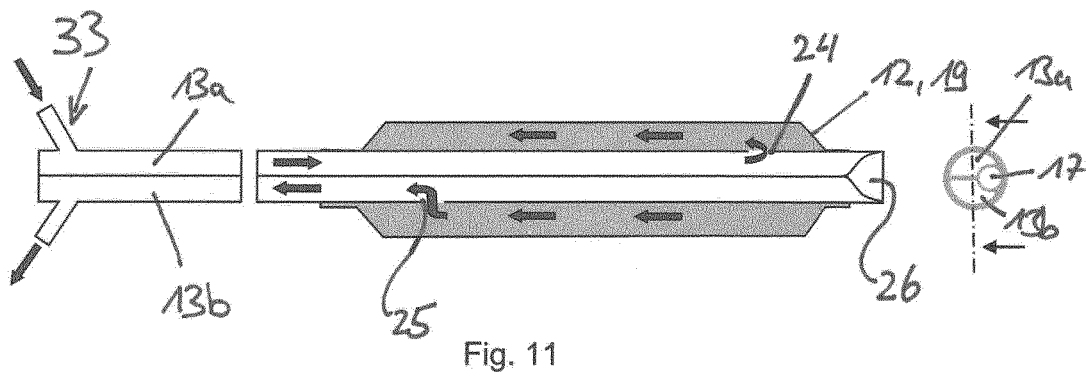
FIG. 11 shows a longitudinal section through the catheter as per FIG. 10.

A further supply means 10, more particularly a catheter, which is suitable for all above-described systems and, as such, is disclosed and claimed together with these, is depicted in FIGS. 10 and 11.

The catheter 10 has a three-lumen cross section. The two temperature control lines 13*a*, 13*b* have an approximately kidney-shaped embodiment in terms of their cross section and partly surround the channel 17, which has a circular cross section. The channel 17 is arranged laterally on the wall of the catheter 10, i.e. eccentrically in the catheter 10. A different subdivision of the lumens is possible. In general, the channel 17 has a smaller cross section than a temperature control line 13*a*, 13*b* in each case.

The channel 17 is suitable for supplying a separate supply line 18, in particular a micro-catheter 18, in particular a 2 Fr micro-catheter. The channel 17 preferably has a diameter from 0.7 mm to 1.1 mm, in particular from 0.8 mm to 1.0 mm, in particular from 0.85 mm to 0.95 mm.

The diameter of the catheter 10, on which the temperature control element 12, in particular the temperature control balloon 19, is attached, is, at least level with the balloon, from 2.0 mm to 2.6 mm, in particular from 2.1 mm to 2.5 mm, in particular from 2.2 mm to 2.4 mm, in particular from 2.25 mm to 2.35 mm.

The temperature control balloon 19 is attached to the distal end of the catheter 10. The temperature control balloon 19 is preferably at a distance from the tip of the catheter 10. The distance can be from 10 mm to 30 mm. A marker (not depicted here) can be arranged at the tip of the catheter 10.

The axial length of the temperature control balloon 19 is preferably from 3 cm to 10 cm, in particular from 4 cm to and 9 cm, in particular from 6 cm to 8 cm. The diameter of the expanded balloon 19 is between 4 mm and 8 mm, in particular between 5 mm and 7 mm, in particular between 5.5 mm and 6.5 mm. The length, at least the implantable length, of the catheter 10 is between 120 mm and 140 mm, in particular between 125 and 135 mm. The micro-catheter 18, which is moved in the channel 17, has a distal diameter between 0.55 and 0.7 mm, in particular between 0.55 and 0.66 mm, wherein the latter values correspond to a range between 1.7 and 2 French.

The micro-catheter 18 can be pushed out of the catheter 10 in such a way that the distal region of the micro-catheter 18 projects beyond the distal region of the cooling catheter 10. The projecting region of the micro-catheter 18 has a length of 10 cm to 30 cm, in particular of 15 and 25 cm.

The projecting region corresponds to the maximum adjustable distance between the distal end of the supply line or the micro-catheter 18 and the distal end of the supply means or the catheter 10, in particular the channel 17.

As depicted in FIG. 11, the temperature control element 12, in particular the temperature control balloon 19 is continuously supplied with coolant by the two temperature control lines 13a, 13b, as a result of which the cooling power is improved. Specifically, the supplying temperature control line 13a is connected through a supply opening 24 to the temperature control element 12. The supply opening 24 is arranged distally. The discharging temperature control line 13b is connected to a proximally arranged discharge opening 25 such that heating of the coolant flowing in the temperature control element 12 is avoided by the coolant to be discharged. Here, a single supply and a single discharge opening 24, 25 are depicted in each case. It is also possible to provide a plurality of supply openings 24 and discharge openings 25 in each case, for example openings arranged distributed along the circumference.

In general, at least one supply or discharge opening 24, 25 is embodied in each case in the temperature control lines 13a, 13b, which opening provides a fluid connection between the respective lines 13a, 13b and the temperature control element 12. In a preferred case, a single opening 24, 25 is embodied per line 13a, 13b. The openings 24, 25 are arranged offset from one another, e.g. offset by 180°, relative to the axis of the temperature control element 12, in particular of the temperature control balloon 19. The openings 24, 25 are in each case arranged near the respective end region of the temperature control balloon 19. A plurality of openings can also be provided in each case for the supply and/or the discharge.

In accordance with FIG. 11, a connection system 33 with two connections for the coolant is provided at the proximal end of the catheter 10, for example a Luer connector, through which coolant can be supplied and/or discharged.

The two temperature control lines 13a, 13b are sealed distally from the supply opening 24, as can be identified in FIG. 11. To this end, the wall of the two temperature control lines 13a, 13b tapers and terminates with the outer wall of the catheter 10 in a fluid-tight manner. Such a seal of the two temperature control lines 13a, 13b is produced in a manner known per se by a distally supplied, appropriately profiled tool, which welds the walls of the temperature control lines 13a, 13b.

The tip of the catheter 10 as per FIG. 11 has an insertion region 26. Alternatively, the two temperature control lines 13a, 13b can be sealed by an adhesive or a resin. The axial ends of the temperature control balloon 19 are fixed, e.g. adhesively bonded or laser welded, to the catheter 10.

If an occlusion apparatus, specifically an aneurysm coil, is used as a treatment apparatus, the coil is adapted in such a way that the latter, after release from the micro-catheter 18, has an external diameter as an expanded overall entity which is greater than the external diameter of the micro-catheter 18, in particular greater than the external diameter of the catheter 10.

LIST OF REFERENCE SIGNS

10 Supply means/catheter
11 Recanalization apparatus
12 Temperature control element
13a,b Temperature control lines
14 Proximal end of the temperature control element
15 Distal end of the temperature control element
16 Distal end of the temperature control line
17 Channel
18 Supply line/micro-catheter
19 Temperature control balloon
20 Outlet opening of the temperature control line
21 Outlet opening of the channel
22 Sealing element
23 Transport wire
24 Supply opening
25 Discharge opening
BG Blood vessel
T Thrombus

The invention claimed is:

1. A medical system for recanalizing a blood vessel at a recanalization site and for controlling an endovascular temperature of blood at a temperature control site, the temperature control site being spaced from the recanalization site, the system comprising:
  a catheter, a recanalization apparatus, a supply line, and a temperature control element; the catheter comprising a channel and a first temperature control line,
    the first temperature control line for flowing a temperature control medium to the temperature control element;
  the supply line being longitudinally moveable inside the channel, the supply line extending from a distal end of the catheter to move the recanalization apparatus to the recanalization sites; and
  the recanalization apparatus comprising an expanded state and a compressed state,
    the recanalization apparatus being radially compressible from the expanded state to the compressed state and being radially expandable from the compressed state to the expanded state, the recanalization apparatus, when in the compressed state, being longitudinally movable inside the supply line and when released from the supply line being in the expanded state at the recanalization site, the temperature control element for controlling the endovascular temperature of blood, the temperature control element being proximal to the recanalization apparatus when the recanalization apparatus is disposed at the recanalization site;

wherein the temperature control element controls the temperature of the blood before the blood flows in the blood vessel from the temperature control element to the recanalization site;

wherein the supply line comprises an extension length of 10 cm to 30 cm extending from a distal end of the catheter, wherein the supply line is configured to extend to the recanalization site.

2. The system as claimed in claim 1, wherein the recanalization apparatus comprises a flow diverter, a thrombectomy apparatus, or an occlusion apparatus.

3. The system as claimed in claim 1, wherein the recanalization apparatus comprises grating structure through which blood can flow in the expanded state, the grating structure being radially compressible from the expanded state to the compressed state and being radially expandable from the compressed state to the expanded state.

4. The system as claimed in claim 1,
further comprising a second temperature control line in the catheter, the second temperature control line and the first temperature control line being connected to the temperature control element for a continuous feed and return of the temperature control medium, or
wherein the first temperature control line is connected to the temperature control element for a pulsating feed and return of the temperature control medium.

5. The system as claimed in claim 1,
further comprising a second temperature control line in the catheter, the second temperature control line and the first temperature control line being connected to the temperature control element for a continuous feed and return of the temperature control medium,
wherein the first temperature control line provides the feed and the second temperature control line is for the return, the first temperature control line is arranged within the second temperature control line.

6. The system as claimed in claim 1,
further comprising a second temperature control line in the catheter, the second temperature control line and the first temperature control line being connected to the temperature control element for a continuous feed and return of the temperature control medium;
wherein the first temperature control line provides the feed and the second temperature control line is for the return, the first temperature control line is arranged within the second temperature control line;
wherein the first temperature control line extends in a distal direction beyond the second temperature control line;
wherein a proximal end of the temperature control element is connected to the second temperature control line and a distal end of the temperature control element is connected to the first temperature control line.

7. The system as claimed in claim 6, wherein at least one outlet opening in the first temperature control line is arranged at the distal end of the temperature control element.

8. The system as claimed in claim 1,
wherein the first temperature control line is connected to the temperature control element for a pulsating feed and return of the temperature control medium;
wherein, in a distal direction, the channel projects beyond the first temperature control line;
wherein a proximal end of the temperature control element is connected to the first temperature control line and a distal end of the temperature control element is connected to the channel.

9. The system as claimed in claim 1, wherein the temperature control element forms a profiled temperature control balloon.

10. The system as claimed in claim 1, wherein the first temperature control line, the second temperature control line, and the channel are coaxial.

11. The system as claimed in claim 1, wherein the supply line comprises the extension length of 15 cm to 25 cm extending from the distal end of the catheter wherein the supply line is configured to extend to the recanalization site.

* * * * *